United States Patent
Lundberg et al.

(10) Patent No.: US 9,180,140 B2
(45) Date of Patent: *Nov. 10, 2015

(54) PERFORMANCE ENHANCING COMPOSITION AND USE THEREOF

(75) Inventors: Jon Lundberg, Djursholm (SE); Eddie Weitzberg, Stockholm (SE)

(73) Assignee: Heartbeet Ltd., Ipswich (GB)

( * ) Notice: Subject to any disclaimer, the term of this patent is extended or adjusted under 35 U.S.C. 154(b) by 189 days.

This patent is subject to a terminal disclaimer.

(21) Appl. No.: 12/528,798

(22) PCT Filed: Feb. 26, 2008

(86) PCT No.: PCT/SE2008/050211
§ 371 (c)(1),
(2), (4) Date: Aug. 26, 2009

(87) PCT Pub. No.: WO2008/105730
PCT Pub. Date: Sep. 4, 2008

(65) Prior Publication Data
US 2010/0047344 A1  Feb. 25, 2010

(30) Foreign Application Priority Data
Feb. 26, 2007 (SE) ........................ 0700520
Mar. 22, 2007 (SE) ........................ 0700729

(51) Int. Cl.
| A61K 33/00 | (2006.01) |
| A23L 1/30 | (2006.01) |
| A23L 1/304 | (2006.01) |
| A23L 2/52 | (2006.01) |
| A61K 45/06 | (2006.01) |
| C01D 9/00 | (2006.01) |
| A61K 36/185 | (2006.01) |

(52) U.S. Cl.
CPC ................. *A61K 33/00* (2013.01); *A23L 1/304* (2013.01); *A23L 1/3014* (2013.01); *A23L 2/52* (2013.01); *A61K 45/06* (2013.01); *A23V 2002/00* (2013.01); *A61K 36/185* (2013.01); *C01D 9/00* (2013.01)

(58) Field of Classification Search
None
See application file for complete search history.

(56) References Cited

U.S. PATENT DOCUMENTS

| 4,868,179 A | 9/1989 | Cohn |
| 6,117,872 A | 9/2000 | Maxwell et al. |
| 2004/0016479 A1* | 1/2004 | Mullay et al. ..................... 149/1 |

(Continued)

FOREIGN PATENT DOCUMENTS

| EP | 0511587 A1 | 11/1992 |
| KR | 2002/0057695 A | 7/2002 |

(Continued)

OTHER PUBLICATIONS

White, Relative Significance of Dietary Sources of Nitrate and Nitrite, J. Agric. Food Chem., vol. 23, No. 5 (1975).*

(Continued)

*Primary Examiner* — Bethany Barham
*Assistant Examiner* — Barbara Frazier
(74) *Attorney, Agent, or Firm* — Porter Wright Morris & Arthur LLP (57) ABSTRACT

The performance of a mammal, manifested as a reduced oxygen uptake ($VO_2$) during physical exercise, can be enhanced by administering to said mammal a non-toxic amount of nitrate and/or nitrite. Liquid, semi-solid and solid snack and food products and nutritional supplements, such as sport drinks are made available.

52 Claims, 5 Drawing Sheets

(56) References Cited

U.S. PATENT DOCUMENTS

| | | |
|---|---|---|
| 2004/0204371 A1 | 10/2004 | Cohn et al. |
| 2005/0266018 A1 | 12/2005 | Boreyko et al. |
| 2006/0182815 A1 | 8/2006 | Gladwin et al. |

FOREIGN PATENT DOCUMENTS

| | | |
|---|---|---|
| WO | WO-99/66921 A1 | 12/1999 |
| WO | 2004/056376 A1 | 7/2004 |
| WO | 2005/004884 A2 | 1/2005 |
| WO | 2006/110601 A2 | 10/2006 |

OTHER PUBLICATIONS

Ogden et al., Mean Body Weight, Height, and Body Weight Index, United States 1960-2002, Advanced Data From Vital and Health Statistics, No. 347 (2004).*

Sies et al., Cocoa polyphenols and inflammatory mediators, Am. J. Clin. Nutr., vol. 81, No. 1, pp. 304S-312S (2005).*

Lacerda et al., Neuroscience Letters, 393, pp. 260-263 (2006).*

Balzer, J. et al. (2007). "Reductase activity of polyphenols?: A commentary on 'Red wine-dependent reduction of nitrite to nitric oxide in the stomach'," *Free Radical Biology and Medicine* 43:1226-1228.

Deng, X.-S. et al. (2004). "Formation of ethyl nitrite in vivo after ethanol administration," *Alcohol* 34:217-223.

Gago, B. et al. (2007). "Red wine-dependent reduction of nitrite to nitric oxide in the stomach," *Free Radical Biology and Medicine* 43:1233-1242.

Grossi, L. and Strazzi, S. (1999). "A New Synthesis of Alkyl Nitrites: The Reaction of Alkyl Alcohols with Nitric Oxide in Organic Solvents," *Journal of Organic Chemistry* 64:8076-8079.

International Search Report mailed on Jun. 12, 2008, for PCT Application No. PCT/SE2008/050211 filed on Feb. 26, 2008, 7 pages.

International Written Opinion mailed on Jun. 12, 2008, for PCT Application No. PCT/SE2008/050211 filed on Feb. 26, 2008, 12 pages.

Jungersten, L. et al. (1997). "Both physical fitness and acute exercise regulate nitric oxide formation in healthy humans," *Journal of Applied Physiology* 82:760-764.

Lundberg, J. O. and Govoni, M. (2004). "Inorganic nitrate is a possible source for systemic generation of nitric oxide," *Free Radical Biology and Medicine* 37(3):395-400.

Peri, L. et al. (2005). "Apples increase nitric oxide production by human saliva at the acidic pH of the stomach: A new biological function for polyphenols with a catechol group?," *Free Radical Biology and Medicine* 39:668-681.

Stamler et al., "Biochemistry of Nitric Oxide and Its Redox-Activated Forms", Science, vol. 258, Dec. 18, 1992, pp. 1898-1902.

Official Action from European Application No. 08 712 840.4 dated Feb. 27, 2014.

Cohn, et al., A Comparison of Enalapril with Hydralazine-Isosorbide Dinitrate in the Treatment of Chronic Congestive Heart Failure, The New England Journal of Medicine, 325:303-310 (1991).

Larsen et al, "Effects of dietary nitrate on oxygen cost during exercise", Acta Physiol (Oxf), 191(1):59-66 (Sep. 2007).

Larsen et al, "Dietary inorganic nitrate improves mitochondrial efficiency in humans", Cell Metab., 13(2):149-159 (Feb. 2011).

Liu et al, "No effect of short-term arginine supplementation on nitric oxide production, metabolism and performance in intermittent exercise in athletes", J Nutr Biochem 20 (6):462-468 (2008).

Bescos, "Effects of dietary L-Arginine intake on cardiorespiratory and metabolic adaptation in athletes", Int J Sport Nutr Exerc Metab, 19:355-65 (2009).

Olek et al, "A single oral intake of arginine does not affect performance during repeated Wingate anaerobic test", J Sports Med Phys Fitness, 50(1):52-56 (2010).

Sunderland et al, "VO2max and ventilator threshold of trained cyclists are not affected by 28-day l-arginine supplementation", J Strength Cond Res, 25 (3):833-837 (2011).

Bailey et al, "Dietary nitrate supplementation reduces the O2 cost of low-intensity exercise and enhances tolerance to high-intensity exercise in humans", J Appl Physiol., 107(4):1144-1155 (2009).

Kelly et al, "Effects of short-term dietary nitrate supplementation on blood pressure, O2 uptake kinetics, and muscle and cognitive function in older adults", Am J Physiol Regul Integr Comp Physiol., 304(2):R73-83 (2013).

Lansley et al, "Dietary nitrate supplementation reduces the O2 cost of walking and running: a placebo-controlled study", J Appl Physiol., 110(3):591-600 (2011).

Vahatalo et al, "No effect of acute L-arginine supplementation on O(2) cost or exercise tolerance", Eur J Appl Physiol. (Feb. 20, 2013).

Nisoli et al, "Mitochondrial biogenesis in mammals: the role of endogenous nitric oxide", Science, 299(5608):896-899 (2003).

Crawford et al, International Journal of Cardiology, 1(3-4):307-314, (1982).

Shen et al, Circulation Research, 75(6):1086-1095 (1994).

McKnight et al, Gut, 40:211-214 (1997).

Bohuslavs'kyi, Fiziol Zh, 51(1):33-42 (2005), Abstract only.

Third Party Observations, filed Apr. 28, 2015 in corresponding EP 08712839.3.

Third Party Observations, filed Apr. 10, 2015 in corresponding EP 08712839.3.

Bescos et al., The Effect of Nitric-Oxide-Related Supplements on Human Performance, Sports Med, 42 (2):99-117 (2012).

* cited by examiner

PERFORMANCE ENHANCING COMPOSITION AND USE THEREOF

CROSS REFERENCE TO RELATED APPLICATIONS

This is a U.S. National Phase patent application of PCT/SE2008/050211, filed Feb. 26, 2008, which claims priority to Swedish patent application Serial No. 0700520-0, filed Feb. 26, 2007, and Swedish patent application Serial No. 0700729-7, filed Mar. 22, 2007, all of which are hereby incorporated by reference in the present disclosure in their entirety.

FIELD OF THE INVENTION

The present invention relates to the field of performance enhancing nutritional foods and food supplements, liquid and solid edible products such as sport drinks, energy drinks and energy bars.

BACKGROUND

It is currently believed that improved sports performance can be attained by the intake of so-called sport drinks. These are usually non-carbonated and frequently contain fructose or other sugars, and complex carbohydrates, which are easily absorbed by the body, and are designed to promote the availability of energy and/or prevent or treat mild dehydration. Sport drinks also contain electrolytes (mainly sodium and potassium salts) and nutrients (proteins and amino acids). Sport drinks, energy drinks and other liquid, semi-solid and solid products, while marketed for athletes, are also consumed by non-athletes, as a snack, in situations where extra energy and endurance is desired.

Sometimes a distinction is made between sport drinks and energy drinks, the former tending to be more isotonic, and the latter containing more sugar and frequently also caffeine. In this context, no such distinction is intended, and the term "performance enhancing food or food supplement" includes sport drinks and energy drinks, as well as other liquid, semi-solid or solid forms, such as energy bars, tablets etc. as described in further detail below.

Physiological adaptation to exercise however involves major cardiovascular and metabolic changes. Oxygen consumption increases dramatically in the active muscles with a parallel increase in muscle blood flow. In these processes the endogenous gas nitric oxide (NO) plays an important regulatory role. NO increases blood flow to the muscles and modulates muscular contraction and glucose uptake (for review see STAMLER, J S. et al. Physiology of nitric oxide in skeletal muscle. Physiol Rev. 2001, vol. 81, no. 1, p. 209-37).

In addition, NO is involved in control of cellular respiration through interaction with enzymes of the mitochondrial respiratory chain (for review see MONCADA, S, et al. Does nitric oxide modulate mitochondrial energy generation and apoptosis?. Nat Rev Mol Cell Biol. 2002, vol. 3, no. 3, p. 214-20).

In vitro studies published in the 1990s show that NO is a modulator of mitochondrial respiration via reversible inhibition of cytochrome c oxidase (CARR, G J. et al. Nitric oxide formed by nitrite reductase of *Paracoccus denitrificans* is sufficiently stable to inhibit cytochrome oxidase activity and is reduced by its reductase under aerobic conditions. Biochim Biophys Acta. 15 May 1990, vol. 1017, no. 1, p. 57-62.; BOLANOS, J P, et al. Nitric oxide-mediated inhibition of the mitochondrial respiratory chain in cultured astrocytes. J. Neurochem. 1994, vol. 63, no. 2, p. 910-6; BROWN, G C, et al. Nanomolar concentrations of nitric oxide reversibly inhibit synaptosomal respiration by competing with oxygen at cytochrome oxidase. FEBS Lett. 19 Dec. 1994, vol. 356, no. 2-3, p. 295-8; CLEETER, M W, et al. Reversible inhibition of cytochrome c oxidase, the terminal enzyme of the mitochondrial respiratory chain, by nitric oxide. Implications for neurodegenerative diseases. FEBS Lett. 23 May 1994, vol. 345, no. 1, p. 50-4; and SCHWEIZER, M, et al. Nitric oxide potently and reversibly deenergizes mitochondria at low oxygen tension. Biochem Biophys Res Comm. 1994, no. 204, p. 169-75).

NO may also interact at other sites of the mitochondrial respiratory chain and in the Krebs cycle (for review see Moncada, supra). While this important action of NO has been very well characterised in cell cultures, less is known about its physiological relevance in vivo and the effects of NO on cellular respiration during physical exercise. Shen and colleagues showed that administration of NOS-inhibitors in vivo during submaximal exercise leads to increased oxygen consumption in dogs (SHEN, W. et al. Role of NO in the regulation of oxygen consumption in conscious dogs. Circulation Res. 1999, no. 84, p. 840-5) and Lacerda and colleagues showed similar results in rats (LACERDA, A C R, et al. Evidence that brain nitric oxide inhibition increases metabolic cost of exercise, reducing running performance in rats. Neuroscience Letters. 2006, no. 393, p. 260-3). The majority of studies have been done using NOS-inhibitors while the effects of administering exogenous NO on exercise are largely unknown. In addition, studies in healthy humans are scarce.

The classical means by which NO production occurs is the L-arginine pathway, where NO is synthesized by specific enzymes, the NO-synthases. A fundamentally different alternative way of generating NO has been described more recently (LUNDBERG, J O, et al. Intragastric nitric oxide production in humans: measurements in expelled air. Gut. 1994, vol. 35, no. 11, p. 1543-6; BENJAMIN, N, et al. Stomach NO synthesis. Nature. 7 Apr. 1994, vol. 368, no. 6471, p. 502; ZWEIER, J L, et al. Enzyme-independent formation of nitric oxide in biological tissues. Nat Med. 1995, vol. 1, no. 8, p. 804-9; and WEITZBERG, E, et al. Nonenzymatic nitric oxide production in humans. NO Biol. Chem. 1998, no. 2, p. 1-7). In this NOS-independent pathway the inorganic anions nitrate ($NO_3-$) and nitrite ($NO_2-$) are reduced in vivo to form NO. Dietary nitrate (found mainly in green leafy vegetables) (MCKNIGHT, G M. Chemical synthesis of nitric oxide in the stomach from dietary nitrate in humans. Gut. 1997, no. 40, p. 211-214; and Weitzberg, 1998, supra) is absorbed from the circulation by the salivary glands, secreted in saliva and partly converted to nitrite in the oral cavity by nitrate reducing bacteria. Swallowed nitrite can then enter the systemic circulation. Indeed, a recent study shows that ingestion of nitrate results in a sustained increase in circulating nitrite levels (LUNDBERG, J O, et al. Inorganic nitrate is a possible source for systemic generation of nitric oxide. Free Rad Bio Med. 2004, vol. 37, no. 3, p. 395-400). Further reduction of nitrite into bioactive NO can occur spontaneously in acidic or reducing environments (Benjamin et al. 1994, supra, Lundberg et al. 1994, supra) but is also greatly enhanced by various proteins and enzymes including deoxyhemoglobin in blood (COSBY, K, et al. Nitrite reduction to nitric oxide by deoxyhemoglobin vasodilates the human circulation. Nat Med. 2003, vol. 9, no. 12, p. 1498-505), deoxymyoglobin (SHIVA, S. et al. Deoxymyoglobin is a Nitrite Reductase That Generates Nitric Oxide and Regulates Mitochondrial Respiration. Circ Res. 9 Feb. 2007), xanthine oxidase (MILLAR, T M, et al. Xanthine oxidoreductase catalyses the reduction of nitrates and nitrite to nitric oxide under hypoxic conditions. FEBS Lett. 8 May 1998, vol. 427, no. 2, p. 225-8) and possibly by enzymes of the mitochondrial respiratory chain (for review see LUNDBERG, J O, et al. Nitrate, bacteria and human health. Nat Rev Microbiol. 2004, vol. 2, no. 7, p. 593-602; LUNDBERG, J O, et al. NO generation from nitrite and its role in vascular control. Arterioscler Thromb Vasc Biol. 2005, vol. 25, no. 5, p. 915-22; and GLADWIN, M T, et al. The emerging biology of the nitrite anion. Nat Chem. Biol. 2005, vol. 1, no. 6, p. 308-14). NOS-independent NO production seems to complement the endogenous NO production especially during ischemia and acidosis when oxygen availability is low and the NO synthases operate poorly (Zweier et al. 1995, supra; Weitzberg et al, 1998, supra; DURANSKI, M R, et al. Cytoprotective effects of nitrite during in vivo ischemia-reperfusion of the heart and liver. J Clin Invest. 2005, vol. 115, no. 5, p. 1232-40; Lundberg et al, 2004, supra). Tissue acidosis and relative hypoxia is present also during physical exercise and in this metabolic state, bioactivation of nitrite is likely enhanced.

The available information on the role of NO in healthy subjects and in particular in athletes during work or exercise is both insufficient and contradictory. Interestingly, the marketing of some currently available food supplements for athletes and bodybuilders refer to the vasodilatory effect of NO. One example is "NOX2" (Bodyonics, Ltd., USA), a product said to contain arginine alpha-ketoglutarate (A-AKG) and arginine-ketoisocaproate (A-KIC) and allegedly capable of boosting short term nitric oxide levels. Other products contain L-arginine, from which NO is synthesized by the NOS enzymes, and the beneficial effects of NO are often referred to, however without offering more detailed explanations.

The relation between peak work rate and resting levels of nitrate in plasma and urine from subjects with different levels of physical fitness has been studied (Jungersten et al., Both physical fitness and acute exercise regulate nitric oxide formation in healthy humans. J Appl Physiol 82:760-764, 1997). A positive relationship between physical fitness and formation of NO at rest was found and it was hypothesised that this positive relationship helps to explain the beneficial effects of physical exercise on cardiovascular health. In Jungerstens study nitrate was used solely as a marker of NO production and the authors state several times that nitrate is a stable and inert end product of NO and that it is biologically inactive.

The present inventors set out to test if administration of dietary nitrate would lead to increased systemic storage pools of nitrite and if this dietary strategy would have an impact on various physiological and biochemical parameters during exercise.

SUMMARY OF THE INVENTION

The inventors surprisingly found that the performance of a mammal manifested as a reduced oxygen uptake ($VO_2$) during exercise was enhanced by administering to said mammal a non-toxic amount of nitrate and/or nitrite. Based on this finding, the inventors make available uses, compositions and methods as defined in the claims, incorporated herein by reference.

SHORT DESCRIPTION OF THE FIGURES

The invention will be described in closer detail in the following description, examples and non-limiting claims, with reference to the attached drawings in which:

DETAILED DESCRIPTION

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

The term "edible" in this context means non-toxic and possible to ingest, however not limited to particular modes of ingesting, such as drinking, chewing, applying to the oral cavity in various forms, such as, for example a spray or aerosol.

The term "functional food" relates to any fresh or processed food claimed to have a health-promoting and/or disease-preventing property beyond the basic nutritional function of supplying nutrients. Functional foods are sometimes called nutraceuticals. The general category includes processed food made from functional food ingredients, or fortified with health-promoting additives, like "vitamin-enriched" products, and also, fresh foods (e g vegetables) that have specific claims attached. Fermented foods with live cultures are often also considered to be functional foods with probiotic benefits.

The present inventors showed that dietary supplementation with inorganic nitrate results in a reduced $VO_2$ during physical exercise and a significant increase in muscular efficiency. These effects occurred without any increase in plasma lactate.

Based on their findings, the present inventors make available a composition, preferably an edible composition, capable of enhancing performance manifested as a reduced oxygen uptake ($VO_2$) during physical exercise when ingested by a mammal, wherein said composition comprises inorganic nitrate and/or nitrite, and in particular a composition wherein the effect of enhanced performance is manifested as both a reduced oxygen uptake ($VO_2$) during physical work and a significant increase in muscular efficiency.

According to one embodiment, nitrate and nitrite are given in a dose ratio interval of about 5:1 to about 100:1 (nitrate:nitrite), such as 5:1, 10:1, 30:1, 50:1, 70:1 and 100:1. Preferably the dose ratio is about 10:1.

According to a particular embodiment, said composition comprises nitrite alone, without the presence of nitrate.

According to another embodiment, said composition in addition to nitrate and/or nitrite, also comprises arginine.

In another embodiment of the present invention non-pathogenic bacteria are added to the nitrate and/or nitrite-comprising composition or the composition containing a blend of nitrate/nitrite-rich and polyphenol-rich compounds as described below. The purpose is to further enhance the generation of bioactive compounds such as NO, nitroso adducts or chemically related compounds. This enhancement will also occur locally in the GI (gastrointestinal) tract via bacteria-dependent reduction of nitrate and nitrite to NO and other bioactive nitrogen oxides. In addition, the compounds formed can be absorbed systemically and have sustained biological effects for example in reducing blood pressure and in preventing atherosclerosis, cancer or any other effect related to enhanced NO release. The composition with added bacteria can be in the form of a drink such as a juice, a yoghurt, a milk based drink or any other fermented food product. The composition with added bacteria can also be included in different types of functional food. Suitable bacteria are the so called probiotic bacteria, included but not limited to *Lactobacilli* (for example *L. acidophilus, L. delbrueckii, L. helveticus, L. salivarius, L. casei, L. curvatus, L. plantarum, L. sakei, L. brevis, L. buchneri, L. fermentum, L. reuteri*) and *Bifidobacteria* species, for example, but not limited to, *B. breve, B. bifidum, B. lactis*) and probiotic yeasts such a *Saccharomyces boulardii*. Suitable non-pathogenic bacteria are for example, but not limited to, *Staphylococcus* species, *Actinomyces* species and *Rothia* species. These microorganisms may also be included in "dry form" for example in tablets, capsules, bars an alike.

According to an embodiment of the invention, the source of inorganic nitrate and nitrite is chosen among a concentrate or an extract of nitrate or nitrite containing plants, vegetables, or fruits or an inorganic nitrate salt. Examples of nitrate and nitrite salts include but are not limited to sodium, potassium, calcium, zinc, arginine, and ammonium. Sodium and potassium salts are presently most preferred. The nitrite and nitrate salts may be of synthetic origin, but may also be isolated from natural sources. Examples of vegetables rich in nitrates are green leafy vegetables, spinach, beetroot, fennel, lettuce, cabbage, Chinese cabbage and the like. Juices, pastes, concentrates etc of such vegetables are contemplated as suitable sources of nitrate. In one embodiment the nitrate in the inventive composition originates from beetroot.

Figure 1:
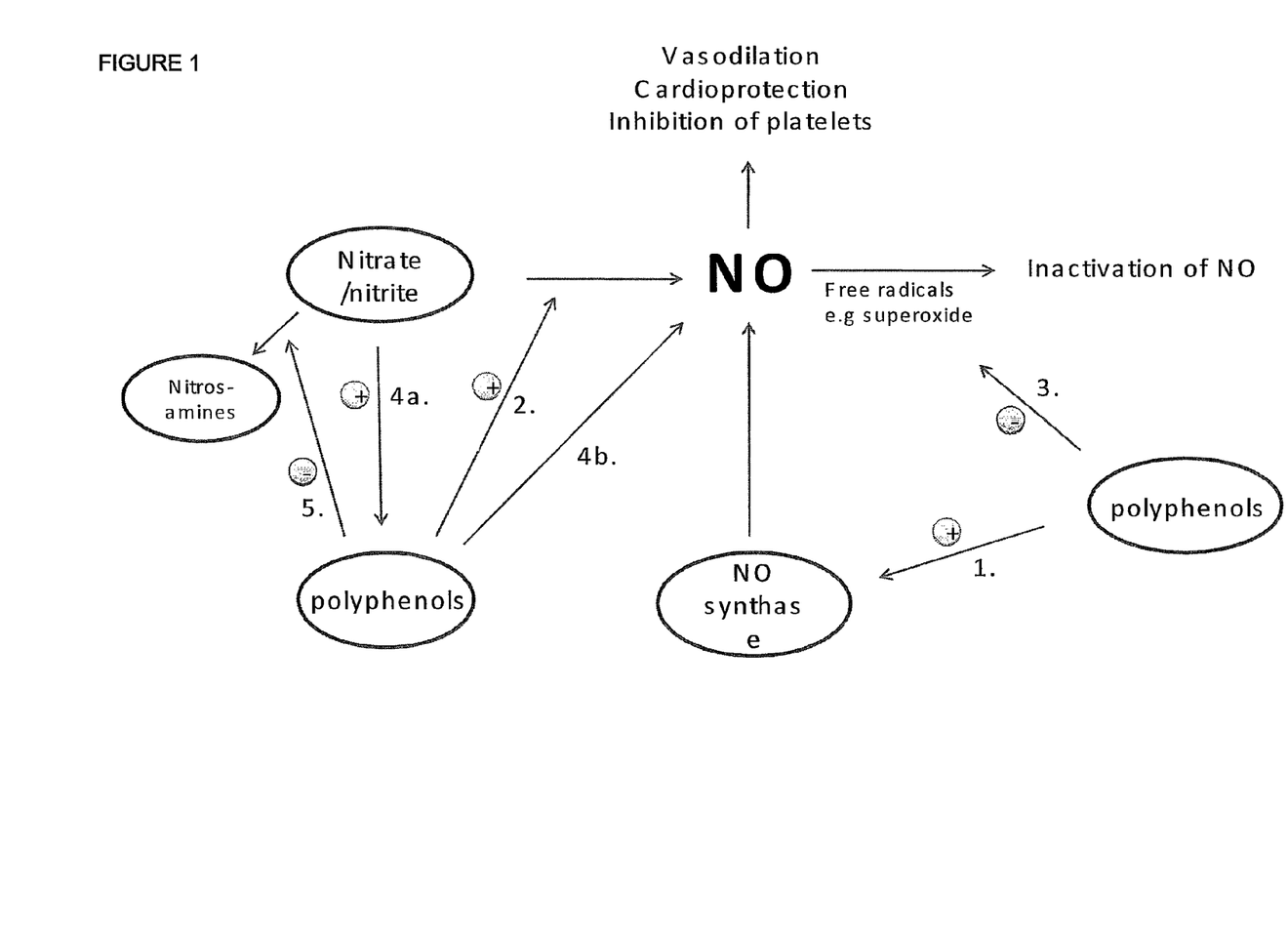
FIG. 1 shows a graph illustrating numerous ways in which the combination of nitrate and polyphenols synergistically act to increase the bioavailability of nitric oxide and at the same time to reduce the formation of harmful compounds such as oxygen radicals and nitrosamines. For detailed explanation see text below.

Many vegetables and fruits are rich in polyphenols. Polyphenols are a group of chemical substances found in plants, characterized by the presence of more than one phenol group per molecule. Polyphenols are generally further subdivided into hydrolyzable tannins, which are gallic acid esters of glucose and other sugars; and phenylpropanoids, such as lignins, flavonoids, and condensed tannins. Thus, in one embodiment of the present invention the nitrate and/or nitrite comprising composition is mixed with a compound that contains high levels of polyphenols. The ratio nitrate comprising composition:polyphenol-rich compound should be chosen to obtain enough supply of nitrate. The nitrate and/or nitrite comprising composition should therefore be at least about 10%, preferably at least about 20%, more preferably at least about 30%, even more preferably at least about 40% and most preferably at least about 50% or even more. It is contemplated that this combined product will have synergistic health promoting effects via potentiation of NO bioavailability. Polyphenols will enhance NO generation by several separate mechanisms highlighted in FIG. 1. First, such agents can directly stimulate endogenous NO formation from NO synthase enzymes (1 in FIG. 1). Second, it is contemplated that these compounds will enhance the reduction of nitrite to bioactive NO due to the presence of reductive —OH groups on the phenol ring (2 in FIG. 1). Third, by acting as scavengers of free radicals such as superoxide, they prevent these radicals from interacting with (and destroying) NO and thereby NO becomes more long-lived (3 in FIG. 1). In addition to this, nitrite or its reaction products can interact with the polyphenol itself and modify it chemically via nitration or nitrosation reactions (4a in FIG. 1). The resulting compound can act as a long-lived NO donor (4b in FIG. 1). An additional effect is that the presence of polyphenols will divert the chemical reactions away from formation of potentially carcinogenic nitrosamines (5 in FIG. 1). Nitrates reaction product nitrite can react with amines to form nitrosamines but polyphenols will inhibit this reaction by a dual mechanism. First they help to rapidly reduce $HNO_2$ directly to NO thereby minimizing the formation of nitrosating species ($N_2O_3$, $HNO_2$). Second, they can directly compete for nitrosation with the amines by being nitrosated themselves.

Examples of fruit and fruit juices rich in polyphenols include, but are not limited to, apple, pear, grapes, lemon, orange, lime, peach, pomegranate, grapefruit, kiwi, ginger and pineapple. Berries and juice from berries are also usable including, but not limited to, blackberries, black raspberries, blueberries, cranberries, red raspberries, cherries, bog wortleberry, lingonberries, black elderberry, black chokeberry, black currant, blueberry, cloudberries and strawberries. Other natural sources of polyphenols include, but are not limited to, vegetables such as carrots, chili, rhubarb, onions. In addition, cacao products (rich in flavanols), green or black tea, nuts, Yerba mate and coffee are all rich in polyphenols. It is contemplated that the combination of nitrate and a polyphenol rich product as described above will act synergistically to enhance NO formation in the body at the expense of detrimental compounds such as nitrosamines. The beneficial effects of this include i.a. a reduction in blood pressure. In one preferred embodiment the nitrate in the inventive composition originates from beetroot (such as beetroot juice) which is blended with one or several polyphenol-rich products. The ratio beetroot juice:polyphenol-rich compound should be chosen to obtain enough supply of nitrate and therefore the beetroot juice part should be at least about 10%, preferably at least about 20%, more preferably at least about 30%, even more preferably at least about 40% and most preferably at least about 50%.

In another embodiment a low concentration of ethanol is added to the inventive composition. It has surprisingly been found that ethanol even in very low concentrations can generate the potent vasodilator ethyl nitrite following reaction with physiological amounts of nitrite. The reaction is enhanced at acidic conditions such as in the gastric lumen. It is contemplated that ingestion of nitrate will lead to accumulation of nitrite in the saliva and the nitrite will react with ethanol in the stomach thereby forming ethyl nitrite. For example, if the inventive composition is in the form of a liquid the ethanol content should be below about 5% (v/v), more preferably below about 2% (v/v), and most preferable between about 0.5-1% (v/v).

In yet another embodiment of the present invention a nitrate or nitrite salt (for example potassium nitrate or ammonium nitrate) or a natural nitrate source including a dried vegetable powder, is combined with liquorice for example in liquorice candies such as salty liquorice (ammonium chloride). The addition of polyphenols to this combination is also preferred. Liquorice is well known for its blood pressure elevating effects and it is contemplated that the addition of nitrate/nitrite alone or in combination with a polyphenol will counteract this via the NO-mediated blood pressure lowering effect of these compounds. In particular a salt such as potassium nitrate, sodium nitrate or ammonium nitrate may be used to replace in part or in whole the salt content (such as sodium chloride or ammonium chloride) of the liquorice product.

The inventive composition preferably has the form of a liquid, a paste, a bar, a cake, a powder, a granulate, an effervescent tablet, a chewing gum, a tablet, a capsule, a lozenge, a fast melting tablet or wafer, a sublingual tablet or a spray. Another composition is a nicotine-free smokeless tobacco and/or wet snuff. Such products can be manufactured using conventional methods practised in the food and beverage industry, or in pharmaceutical industry.

More preferably said composition is in the form of, or constitutes a part of, a food product, such as a liquid, a paste, a bar, a cake, a powder, or a granulate.

According to a preferred embodiment, the composition according to the invention is prepared as a fermented food product, such as a yogurt or similar dairy or non-dairy product, comprising a source of nitrate and/or nitrite in addition to live bacteria capable of enhancing nitrate or nitrite reduction.

The present inventors consider presenting the composition to the market in the form of a sport drink, an energy drink, a sport bar, or an energy bar.

The energy bar may take on a variety of forms. For convenience, it is preferred that the energy food product be shaped like a box, square, cylinder, string, pie, sphere, triangle, or other format suitable for packaging, transportation, handling and eating.

According to another embodiment, the composition is presented to the market as a functional food product.

Products comprising the inventive composition can easily be manufactured by persons skilled in the food, sweets and beverage industry or the pharmaceutical industry, and existing compositions supplemented with nitrate, nitrite and other combinations described herein in amounts according to this invention.

For example an energy bar according to the present invention may include, in addition to nitrate and optionally nitrite, also a variety of other components such as, for example, nuts, crisps, fruit pieces, chocolate, seeds, and the like. Preferred nuts are almonds, peanuts, hazelnuts, cashews, walnuts, pecans, brazil nuts, and the like. Crisp components include rice crisps, corn crisps, oats, wheat flakes, and the like. The chocolate can be any type of chocolate or chocolate like edible component in various forms, such as, for example, chocolate chips, chunks, flakes and the like. Non-limiting examples of seeds include sesame, sun flower, poppy, caraway, fennel and the like.

In one embodiment of the present invention a cacao product such as dark chocolate that is rich in flavanols is combined with a nitrate/nitrite-rich natural compound in a drink or a chocolate bar. One preferred nitrate-rich compound in this embodiment is rhubarb. Again, the nitrate will potentiate the effect of the flavanols via enhancement of NO formation as described above and in FIG. 1.

Additionally, traditional food ingredients such as flavours and the like may be included. For example, additional ingredients may include natural and artificial flavours, sweeteners, salt, flavour enhancers, colour additives, emulsifiers, stabilizers, fats, preservatives, and the like.

Contamination of a nitrate/nitrite-containing food or drink with unwanted bacteria may result in a large accumulation of nitrite, due to nitrate reducing bacterial enzymes. Ingestion of high levels of nitrite may cause potentially serious methemoglobinemia. In one embodiment a nitrate-rich composition is mixed with a compound that inhibits unwanted bacterial growth. Such compound should be chosen so as not to affect the taste of the product negatively. Ideally, it should enhance the taste and at the same time increase the bioactivity of the product. One option is to acidify the inventive composition so that final pH is below about 5, and most preferably between about pH 2-4. This will inhibit and/or abolish bacterial growth. Suitable acidifying agents can be any agent that reduces pH and include artificial compounds as well as natural juices from e.g., but not limited to, lemon or lime, ascorbic acid, acetic acid or vinegar (from apple, grapes or other fruits). It is contemplated that with the use of natural products a dual effect is achieved. Besides having an antibacterial effect, they are rich in polyphenols, which enhance the generation of bioactive NO from nitrate/nitrite in the vegetable drink. In one particular embodiment a nitrate-rich vegetable juice (e.g. beetroot juice) is mixed with a compound that inhibits bacterial growth.

The present invention also makes available a second non-medical use of inorganic nitrate and/or nitrite, i.e. for the manufacture of a composition for enhancing the performance of a mammal wherein the effect of enhancing performance is manifested as reduced $VO_2$ during physical exercise.

Preferably the effect of enhancing performance is manifested as both a reduced $VO_2$ during physical exercise and a significant increase in muscular efficiency.

According to an embodiment of the above use, nitrate and nitrite is used in a dose ratio interval of about 5:1 to about 100:1 (nitrate:nitrite), such as 5:1, 10:1, 30:1, 50:1, 70:1 and 100:1. Preferably the dose ratio is about 10:1.

According to a particular embodiment, said inorganic nitrite is used alone, without the presence of nitrate.

According to an embodiment of the invention, the source of inorganic nitrate/nitrite is chosen among a concentrate or an extract of nitrate containing vegetables, or an inorganic nitrate or nitrite salt. Examples of nitrate and nitrite salts include but are not limited to sodium, potassium, calcium, zinc, arginine, and ammonium. Examples of vegetables rich in nitrates are green leafy vegetables, spinach, beetroot, fennel, lettuce, cabbage and the like. Juices, pastes, concentrates etc of such vegetables are contemplated as suitable sources of nitrate.

Combinations of nitrate and nitrite salts can also be used. According to one embodiment, nitrate and nitrite are given orally in a dose ratio interval of about 5:1 to about 100:1 (nitrate:nitrite), such as 5:1, 10:1, 30:1, 50:1, 70:1 and 100:1. Preferably the dose ratio is about 10:1. This will provide the acute effects of the nitrite as soon as it is absorbed, and then provide a sustained effect of the nitrate following its bioconversion into nitrite.

In yet another embodiment inorganic nitrate and/or nitrite is used together with polyphenols. The characteristics and health promoting effects of polyphenols are described above. The ratio inorganic nitrate and/or nitrite composition: polyphenol-rich compound should be chosen as to obtain enough supply of nitrate/nitrite. The nitrate/nitrite comprising composition should therefore be at least about 10%, preferably at least about 20%, more preferably at least about 30%, even more preferably at least about 40% and most preferably at least about 50% or even more.

Examples of fruit and fruit juices rich in polyphenols that can be used are, but not limited to, apple, pear, grapes, lemon, orange, lime, peach, pomegranate, grapefruit, kiwi, ginger and pineapple. Berries and juice from berries are also usable such as, but not limited to, blackberries, black raspberries, blueberries, cranberries, red raspberries, cherries, bog wortleberry, lingonberries, black elderberry, black chokeberry, black currant, blueberry, cloudberries and strawberries. Other natural sources of polyphenols include, but are not limited to, vegetables such as carrots, chili, rhubarb, onions. In addition, cacao products (rich in flavanols), green or black tea, nuts, Yerba mate and coffee are all rich in polyphenols. In one preferred embodiment beetroot (such as beetroot juice) is used as a source of inorganic nitrate together with one or several polyphenol-rich products. The ratio beetroot juice: polyphenol-rich compound should be chosen to obtain enough supply of nitrate and therefore the beetroot juice part should be at least about 10%, preferably at least about 20%, more preferably at least about 30%, even more preferably at least about 40% and most preferably at least about 50%.

In another embodiment of the present invention non-pathogenic bacteria are used in combination with inorganic nitrate and/or nitrite or the composition containing a blend of inorganic nitrate and/or nitrite and polyphenol-rich compounds. The combination with bacteria can be in the form of a drink such as a juice, a yoghurt, a milk based drink or any other fermented food product. The combination with bacteria can also be included in different types of functional food products. Suitable bacteria are the so called probiotic bacteria, included but not limited to *Lactobacilli* (for example *L. acidophilus, L. delbrueckii, L. helveticus, L. salivarius, L. casei, L. curvatus, L. plantarum, L. sakei, L. brevis, L. buchneri, L. fermentum, L. reuteri*) and *bifidobacteria* species, for example, but not limited to, *B. breve, B. bifidum, B. lactis*) and probiotic yeasts such a *Saccharomyces boulardii*. Suitable non-pathogenic bacteria are for example, but not limited to, *Staphylococcus* species, *Actinomyces* species and *Rothia* species. These microorganisms may also be used in "dry form".

Contamination of a nitrate-containing food or drink with bacteria may result in a large accumulation of nitrite, due to nitrate reducing bacterial enzymes. Ingestion of high levels of nitrite may cause potentially serious methemoglobinemia. In one embodiment a nitrate-rich composition is used together with a compound that inhibits bacterial growth. Such compound should be chosen so as not to affect the taste of the product negatively. Ideally, it should enhance the taste and at the same time increase the bioactivity of the product. One option is to acidify the juice so that final pH is below about 5, and most preferably between about pH 2-4. This will inhibit and/or abolish bacterial growth. Suitable acidifying agents can be any agent that reduces pH and include artificial compounds as well as natural juices from e.g., but not limited to, lemon or lime, ascorbic acid, acetic acid or vinegar (from apple, grapes or other fruits). It is contemplated that with the use of natural products a dual effect is achieved. Besides having an antibacterial effect, they are rich in polyphenols, which enhance the generation of bioactive NO from nitrate/nitrite in the vegetable drink. In one particular embodiment a nitrate-rich vegetable juice (e.g. beetroot juice) is used together with a compound that inhibits bacterial growth.

In another embodiment of the present invention a low concentration of ethanol is used together with inorganic nitrate and/or nitrite. For example, if the inventive composition is in the form of a liquid, the ethanol content should be below about 5% (v/v), more preferably below about 2% (v/v), and most preferable between about 0.5-1% (v/v).

In yet another embodiment of the present invention a nitrate and/or nitrite salt (for example potassium nitrate or ammonium nitrate) or a natural nitrate source including a dried vegetable powder, is used in combination with liquorice, for example salty liquorice (ammonium chloride). The use of polyphenols to this combination is also preferred. In particular a salt such as potassium nitrate, sodium nitrate or ammonium nitrate may be used to replace in part or in whole the salt content (such as sodium chloride or ammonium chloride) of the liquorice product.

The composition of the present invention may be manufactured into liquids, pastes, bars, cakes, powders, granulates, effervescent tablets, tablets, capsules, lozenges, chewing gum, fast melting tablets or wafers, sublingual tablets, a spray or the like, using conventional methods practiced in the food, sweets and pharmaceutical industry.

Further the composition may also be manufactured in the form of or as a part of a food product, such as a liquid, a paste a bar, a cake a powder or a granulate. It may for example be in the form of a fermented food product, a functional food product, or a sport drink or the like as mentioned above.

In one embodiment of the present invention an inorganic nitrate and/or nitrite is used in combination with a cacao product such as dark chocolate that is rich in flavanols. One preferred nitrate-rich compound in this embodiment is rhubarb.

In yet another embodiment inorganic nitrate and/or nitrite is used in combination with a compound that inhibits bacterial growth. One option is to acidify the juice so that final pH is below about 5, and most preferably between about pH 2-4. This will inhibit and/or abolish bacterial growth. Suitable acidifying agents can be any agent that reduces pH and include artificial compounds as well as natural juices from e.g., but not limited to, lemon or lime, ascorbic acid, acetic acid or vinegar (from apple, grapes or other fruits). It is contemplated that with the use of natural products a dual effect is achieved. In one particular embodiment a nitrate-rich vegetable juice (e.g. beetroot juice) is used in combination with a compound that inhibits bacterial growth.

The inventors also make available a method for non-therapeutically enhancing the performance of a mammal, wherein inorganic nitrate and/or nitrite is administered to said mammal. Said mammal is chosen among a human, a horse, or a dog, preferably a human. Preferably the dose of nitrate is about 1-1000 umol sodium nitrate/kg bodyweight/day. Correspondingly, the dose of nitrite is preferably about 0.1-100 umol/kg bodyweight/day.

More specifically, for the use of a nitrate salt perorally, a dose of about 0.01-100 mmol/kg/24 h is currently preferred or more preferably a dose of about 0.01-10 mmol/kg/24 h, even more preferably 0.1-1 mmol/kg/24 h. Correspondingly, the dose of nitrite is about 0.001-10 mmol/kg/24 h, preferably about 0.001-1 mmol/kg/24 h and more preferably about 0.0001-0.1 mmol/kg/24 h.

According to an embodiment of the invention, nitrate and nitrite is administered in a dose ratio interval of about 5:1 to about 100:1 (nitrate:nitrite), such as 5:1, 10:1, 30:1, 50:1, 70:1 and 100:1. Preferably the dose ratio is about 10:1.

According to one particular embodiment, only nitrite is administered.

In yet another embodiment of the inventive method inorganic nitrate and/or nitrite is administered together with polyphenols. The characteristics and health promoting effects of polyphenols are described above. The ratio inorganic nitrate and/or nitrite composition:polyphenol-rich compound should be chosen to obtain enough supply of nitrate. The nitrate/nitrite comprising composition should therefore be at least about 10%, preferably at least about 20%, more preferably at least about 30%, even more preferably at least about 40% and most preferably at least about 50% or even more. Examples of products rich in polyphenols that can be administered are outlined above.

In another embodiment of the present invention non-pathogenic bacteria are administered in combination with inorganic nitrate and/or nitrite or the composition containing a blend of inorganic nitrate and/or nitrite and polyphenol-rich compounds. Non-limiting examples of suitable bacteria for administration are outlined above.

In another embodiment of the inventive method inorganic nitrate and/or nitrite is administered together with a low concentration of ethanol. For example, if the inventive inorganic nitrate and/or nitrite composition is in the form of a liquid, the ethanol content should be below about 5% (v/v), more preferably below about 2% (v/v), and most preferable between about 0.5-1% (v/v).

In yet another embodiment of the present invention a nitrate or nitrite salt (for example potassium nitrate or ammonium nitrate) or a natural nitrate source including a dried vegetable powder, is administered in combination with liquorice for example salty liquorice (ammonium chloride). The administration of polyphenols to this combination is also preferred. In particular a salt such as potassium nitrate, sodium nitrate or ammonium nitrate may be used to replace in part or in whole the salt content (such as sodium chloride or ammonium chloride) of the liquorice product.

In one embodiment of the present invention an inorganic nitrate and/or nitrite is administered in combination with a cacao product such as dark chocolate that is rich in flavanols. One preferred nitrate-rich compound in this embodiment is rhubarb.

There is reason to believe that the observed effects of nitrate on physical performance involve initial reduction of nitrate to nitrite. Nitrate itself is believed to be biologically inert and cannot be metabolised by mammalian cells. However, after ingestion nitrate re-enters into the mouth via the salivary glands and is effectively reduced by commensal bacteria thereby forming nitrite. In contrast to nitrate the nitrite ion has recently been shown to possess a wide range of bioactivities.

The inventors noted an increase in plasma nitrite after the nitrate treatment period thereby confirming in vivo reduction of nitrate as described previously (Lundberg & Govoni 2004, LARSEN, F J, et al. Effects of dietary nitrate on blood pressure in healthy volunteers. N Engl J Med. 2006, vol. 255, no. 26, p. 2792-3). Another finding in support of nitrite being bioactive was its effective consumption during exercise in contrast to the unchanged levels of plasma nitrate. Ultimately the bioactivity of nitrite is likely related to its further reduction to NO and possibly other closely related nitrogen intermediates. In addition, it has been recently suggested that nitrite itself may directly affect cellular signalling pathways (BRYAN, N S, et al. Nitrite is a signaling molecule and regulator of gene expression in mammalian tissues. Nat Chem Biol. 2006, vol. 1, no. 5, p. 290-7). Although probably unlikely, at this early stage, effects of the nitrate ion itself cannot be excluded. There are several principle ways by which biological effects of nitrogen oxides may be propagated including alteration of protein function by nitrosylation, nitration or direct binding to protein heme-moieties as in the prototypic activation of guanylyl cyclase by NO.

Earlier studies using NOS inhibitors to block endogenous NO production give some indications. NOS-inhibition has been shown to increase submaximal $VO_2$ in dogs during exercise, independently of the reduction in blood flow (SHEN, W. et al. Nitric oxide. An important signaling mechanism between vascular endothelium and parenchymal cells in the regulation of oxygen consumption. Circulation. 15 Dec. 1995, vol. 92, no. 12, p. 3505-12., ISHIBASHI, Y, et al. ATP-sensitive K+-channels, adenosine and NO-mediated mechanisms account for coronary vasodilation during exercise. Circulation Res. 1998, no. 82, p. 346-359.; Shen et al. 1999, supra). The increase in $VO_2$ during NOS-blockade has been explained by the fact that NO affects tissue respiration by reversible inhibition of the respiratory enzyme cytochrome c oxidase (Carr & Ferguson 1990, supra; Bolanos et al. 1994, supra; Brown & Cooper 1994, Cleeter et al. 1994, Schweizer & Richter 1994). Others have related the increased $VO_2$ during NOS-blockade to an inhibiting effect of NO on proton leakage over the inner mitochondrial membrane (BOHUSLAVS'KYI, A, et al. Effect of nitric oxide on the efficiency of oxygen consumption by the working skeletal muscle in fatigue. Fiziol Zh. 2005, vol. 51, no. 1, p. 33-42; NAVET, R, et al. Proton leak induced by reactive oxygen species produced during in vitro anoxia/reoxygenation in rat skeletal muscle mitochondria. J Bioenerg Biomembr. 2006, vol. 38, no. 1, p. 23-32; WANG, G, et al. Nitric oxide donors protect murine myocardium against infarction via modulation of mitochondrial permeability transition. Am J Physiol Heart Circ Physiol. 2005, vol. 288, no. 3, p. 1290-5). If the effects of nitrate were solely due to inhibition of cytochrome c oxidase one would expect an increase in anaerobic metabolism during physical exercise and a larger accumulation of lactate. However, judging from the results this was not the case, as the plasma lactate concentration was near identical after nitrate supplementation compared to placebo. The inventors consider this to be very surprising.

The studies using NOS inhibitors cited above all imply that endogenous NO is involved in regulation of oxygen consumption but there have been few attempts to study the effect of exogenous NO delivery. Studies with NO-donors such as nitroprusside and nitroglycerine have shown somewhat diverging results, with decreases in $VO_2$ in some cases (RECCHIA, F A, et al. Nitric oxide controls cardiac substrate utilization in the conscious dog. Cardiovasc Res. 1999, no. 44, p. 325-32; LOKE, K E, et al. Nitric oxide modulates mitochondrial respiration in failing human heart. Circulation. 21 Sep. 1999, vol. 100, no. 12, p. 1291-7), no effect in one study (NUNEZ, C, et al. Discrepancies between nitroglycerin and NO-releasing drugs on mitochondrial oxygen consumption, vasoactivity, and the release of NO. Circ Res. 11 Nov. 2005, vol. 97, no. 10, p. 1063-9) and increases in other settings (DE BACKER, D, et al. Effects of dobutamine on the relationship between oxygen consumption and delivery in healthy volunteers: comparison with sodium nitroprusside. Clin Sci (Lond). 1996, vol. 90, no. 2, p. 105-11).

Several of the proposed mechanisms for nitrite reduction to NO described above could theoretically come into play during physical exercise. Thus, all these pathways are greatly enhanced during hypoxia and when pH decreases such as in a working muscle. Shiva and colleagues very recently demonstrated deoxymyoglobin-dependent nitrite reduction to NO in rat heart homogenates with a concomitant inhibition of mitochondrial respiration (Shiva et al 2007, supra). Another possible pathway includes NO formation by the mitochondria themselves (KOZLOV, A V, et al. Nitrite reductase activity is a novel function of mammalian mitochondria. FEBS Lett. 2 Jul. 1999, vol. 454, no. 1-2, p. 127-30) or even simple acidic reduction of nitrite in the working muscle (Zweier et al. 1995, supra, MODIN, A, et al. Nitrite-derived nitric oxide: a possible mediator of 'acidic-metabolic' vasodilation. Acta Physiol Scand. 2001, vol. 171, no. 1, p. 9-16). Cosby and colleagues described NO formation and vasodilation from the reaction of circulating nitrite ions with deoxyhemoglobin in blood (COSBY, K, et al. Nitrite reduction to nitric oxide by deoxyhemoglobin vasodilates the human circulation. Nat. Med. 2003, vol. 9, no. 12, p. 1498-505). While this latter pathway, and possibly also tissue nitrite reduction, very well might explain the recently described nitrate-induced reduction in resting blood pressure (Larsen et al. 2006), it is still not obvious how this NO also would decrease oxygen consumption in the working muscle. Thus, an effective inhibition of mitochondrial respiration e.g. by deoxymyoglobin-derived NO, would again be expected to result in accumulation of plasma lactate which was not the case.

The efficiency of the muscles to produce work has been related to the percentage of type I muscle fibres (COYLE, E F, et al. Cycling efficiency is related to the percentage of type I muscle fibers. Med Sci Sports Exerc. 1992, vol. 24, no. 7, p. 782-8) and uncoupling protein-3 (UCP3) content of muscle fibres (MOGENSEN, M, et al. Cycling efficiency in humans is related to low UCP3 content and to type I fibers but not to mitochondrial efficiency. J Physiol. 2006, vol. 571, no. 3, p. 669-681). Other factors that might contribute to the efficiency of movement are anatomical, biochemical and biomechanical features (WILLIAMS, K R. The relationship between mechanical and physiological energy estimates. Med Sci Sports Exerc. 1985, no. 17, p. 317-25). Thus, simply measuring differences in $VO_2$ at different work rates is not an optimal estimate of muscular efficiency because the energy output for a certain $VO_2$ is dependent upon substrate utilization. Gross efficiency (GE) calculations include possible changes in respiratory exchange ratio and thereby take substrate utilization into account. The improved GE after nitrate supplementation indicates better efficiency, but even so, it cannot be exclude that this improved efficiency originates from reduced baseline energy expenditure (EE). The Delta efficiency (DE) calculations are not dependent on the baseline EE and are also based on all work rates taken together instead of a single work rate at a time as in the GE-calculations. It is therefore plausible to expect DE to be the most valid estimate of muscular efficiency in this case. Indeed, even DE was significantly improved after nitrate supplementation. It is unlikely that the improved efficiency by nitrate comes from mechanical factors. The subjects of this study were all cyclists with many years of experience of training and competing. It is improbable that a few visits to the laboratory would change their efficiency during cycling to any noteworthy extent. Especially since the subjects used the same cycling shoes, clip-on pedals and the same seat position as they where used to during training makes this even more unlikely. More important, the randomization procedure used in this study rules out any such differences. Marcheal and Gailly (MARCHEAL, G, et al. Effects of nitric oxide on the contraction of skeletal muscle. Cell Mol Life Sci. 1999, no. 55, p. 1088-1102) demonstrated a faster relaxing velocity of muscle fibres in in situ experiments during administration of an NO-donor, thereby implicating a neuromuscular modulatory effect of NO. It remains to be proven if this can improve the muscular efficiency during cycling.

The finding that the oxygen pulse at a given work rate decreases by nitrate supplementation is a direct effect of the lower oxygen demand at that work rate. However, there is no difference in oxygen pulse at a given absolute oxygen uptake. The lack of effect of nitrate on $VE/VO_2$ or oxygen pulse indicates that the improved efficiency originates from muscular or mitochondrial adaptations rather than from central adaptations in the heart or the lungs.

In summary, the present findings demonstrate a lower oxygen cost during submaximal work after dietary supplementation with nitrate, in amounts achievable through the intake of a non-toxic amount of nitrite. This occurred without an accompanying increase in plasma lactate, indicating that the energy production had become more efficient. The mechanism of action and main targets need to be clarified but the process likely involves in vivo reduction of nitrate into bioactive nitrogen oxides including nitrite and NO.

EXAMPLES

Methods

Subjects

Nine healthy, well-trained ($VO_{2peak}$ 55+/−3.7 ml×kg$^{-1}$×min$^-$), males (28+/−6 years) volunteered for the study. All subjects were trained cyclists or triathletes and well accustomed to the testing procedure. The inventors in this study chose to use well-trained subjects to avoid training effects from the tests such as enhanced $VO_{2peak}$ or better mechanical efficiency during submaximal exercise. The protocol was approved by the regional ethics committee in Stockholm and all subjects gave their written consent prior to participation.

Dietary Supplementation with Nitrate

The aim with the present study was to investigate the effects of two distinct dietary patterns, one with higher, and one with lower than normal nitrate intake. The study had a double-blind placebo-controlled cross-over design. During two three-day periods, separated by a washout interval of ten days, the subjects were instructed to avoid all foods with moderate or high nitrate content (all vegetables, all cured meats, strawberries, grapes, and tea). In addition, they were told to restrain from alcohol and tobacco products. Otherwise they were free to eat any food they liked during the three days of restricted diet. The subjects were randomized to start with either ingestion of 0.1 mmol sodium nitrate/kg bodyweight/day dissolved in water or an equal amount of sodium chloride (placebo). The daily dose was divided and ingested three times daily. The different solutions could not be distinguished by taste or appearance. The daily nitrate dose corresponded to the amount normally found in 150-250 gram of a nitrate-rich vegetable such as spinach, lettuce or beetroot (Lundberg et al, 2004, supra). The last dose of nitrate or placebo was ingested in the morning on the day of measurement (see the main tests below). The order between the nitrate supplementation period (NIT) and the placebo period (CON) was balanced. During the washout period the subjects did not adhere to any specific dietary regime.

Experimental Protocol

Measurements were carried out on an electrically braked cycle ergometer (Monark 839E, Varberg, Sweden) that was modified with a racing saddle and the pedal system the subjects were familiar with from training. The bicycle ergometer was computer-controlled, permitting a constant work rate regardless of the cadence the subject chose to pedal with. The pedaling cadence was individually chosen in the range of 70-90 rpm but kept constant during the test to minimize differences in work output due to changes in muscle recruitment patterns.

Pulmonary ventilation ($V_E$), oxygen uptake ($VO_2$), $CO_2$ output ($VCO_2$) and respiratory exchange ratio (RER) were measured at 10 second intervals by a computerised gas analyser (AMIS 2001, Odense, Denmark) connected to a flow meter which the subjects breathed through via a mouthpiece and a plastic tube. Heart rate (HR) was continuously recorded during the tests with a portable heart rate monitor (Polar S610, Polar, Kempele, Finland). Capillary blood samples (20 µl) were collected from the fingertip and were analyzed for lactate ([HIa]) using a Biosen C-Line Sport Analyser (EKF diagnostics, Magdeburg, Germany). Haemoglobin concentration ([Hb]) at rest was determined with capillary blood taken from the fingertip and analyzed with an Hb-measuring device (Hemocue, Ängelholm, Sweden). Hematocrit (Hct) was determined by centrifuging capillary blood at 12000 rpm for three minutes.

Pre-Tests:

Each subject attended the laboratory twice within a two week period before the first main tests. The first pre-test was carried out to familiarize the subject with the bicycle ergometer and the testing procedure. The subjects did a preliminary test at five submaximal levels with every level lasting for five minutes. There was no rest between the different submaximal levels. $VO_2$ was continuously measured with the AMIS 2001. At the end of each submaximal level capillary blood was taken from the fingertip and later analysed for [HIa]. At every work rate the subjects rated their perceived exertion on the Borg's RPE-scale (BORG, G. Perceived exertion as an indicator of somatic stress. Scand J Rehabil Med. 1970, vol. 2, no. 2, p. 92-8), both central and muscular exertion were rated. After eight minutes of recovery, the subject was instructed to cycle for as long as possible at a work rate corresponding to his calculated maximal oxygen uptake (ÅSTRAND, P O, et al. Textbook in work physiology. New York: McGraw-Hill Book Company, 1970. p. 619). During this test the subjects actual $VO_{2peak}$ was measured and if the subject was able to cycle for longer than seven minutes extra power of 20-30 watts was added every minute until exhaustion. One and three minutes after the maximal test capillary blood were sampled from the fingertip for analysis of [HIa].

Before the second pre-test, the submaximal levels were adjusted so that they corresponded to 45, 60, 70, 80 and 85% of $VO_{2peak}$. The maximal work rate was also adjusted, if necessary, so that the time to exhaustion was kept between four and seven minutes.

The Main Tests:

The subjects refrained from heavy exercise three days prior to the main tests and avoided all exercise the day before the tests. They were also told to eat their last light meal at least 3 hours before the start of the tests. When the subjects came to the laboratory they received their last dose of either placebo or nitrate and were allowed to rest in the supine position for 60 minutes before the test commenced.

All subjects used a standardised warm up procedure of five min of cycling at 100 watts followed by five minutes of rest. The submaximal and maximal tests were performed in the same way as the second pre-test with five submaximal work rates lasting five minutes each, without rest between the different levels. Identical work rates were used during the two main tests. Venous blood (9 ml) was drawn at rest 45 minutes after the last nitrate/placebo-dose was ingested and again immediately after the $VO_{2peak}$-test. The blood was placed in an ice bath and centrifuged within five minutes at 1300 rpm and 4° C. The plasma was separated and kept at −80° C. until it was analysed for its nitrate and nitrite concentrations by a chemiluminescence assay as described previously (Lundberg 2004, supra).

Statistics and Calculations:

Results are expressed as means+/−standard deviation (mean+/−SD). Paired t-tests were used to evaluate the difference between the nitrate and the placebo trials. The significance level was set as $p=<0.05$.

Gross efficiency (GE) was defined as the work rate divided by the actual energy expenditure (EE). The EE was in turn calculated with the Brouwer equation (BROUWER, E. On simple formulae for calculating the heat expenditure and the quantities of carbohydrate and fat oxidized in metabolism of men and animals, from gaseous exchange (Oxygen intake and carbonic acid output) and urine-N. Acta Physiol Pharmacol Neerl. 1957, no. 6, p. 795-802). Delta efficiency (DE) was defined as the increase in work rate divided by the increase in EE (GAESSER, G A, et al. Muscular efficiency during steady-rate exercise: effect of speed and work rate. J Appl Physiol. 1975, no. 38, p. 1132-1139). The DE was based on the four lowest work rates and was analyzed with linear regression. The oxygen pulse is defined as $VO_2/HR$.

Results:

Blood Pressure at Rest:

Average resting systolic blood pressure was lower after nitrate supplementation (112+/−8 mmHg) compared to placebo (120+/−5.9, p<0.01). The diastolic blood pressure was also lower after nitrate (68+/−5.5 mmHg) compared to placebo (74+/−6.8 mmHg, p<0.01). Parts of these findings have been published as a separate communication (Larsen et al. 2006).

Blood Values:

No change was observed in [Hb] at rest (NIT 152+/−11, CON 153+/−11 g×l$^{-1}$, p=0.87) or immediately after the $VO_{2peak}$-test (NIT 163+/−13, CON 161+/−13 g×l$^{-1}$, p=0.27). Nor were there any change in the hematocrit value at rest (NIT 42+/−4, CON 43+/−3%, p=0.19) or after the $VO_{2peak}$-test (NIT 46+/−4, CON 47+/−4%, p=0.6).

Plasma levels of nitrate at rest were 27+/−6.9 µM in CON and 182+/−55 in NIT (p=<0.01). Nitrate levels immediately after the maximal work test were 29+/−6.1 in CON and 175+/−61 µM in NIT (p=<0.01). Plasma nitrate did not change during exercise either in NIT or in CON (p=0.8). Nitrite levels at rest were 124+/−28 in CON and 226+/−87 nM in NIT (p=<0.01).

Figure 2:
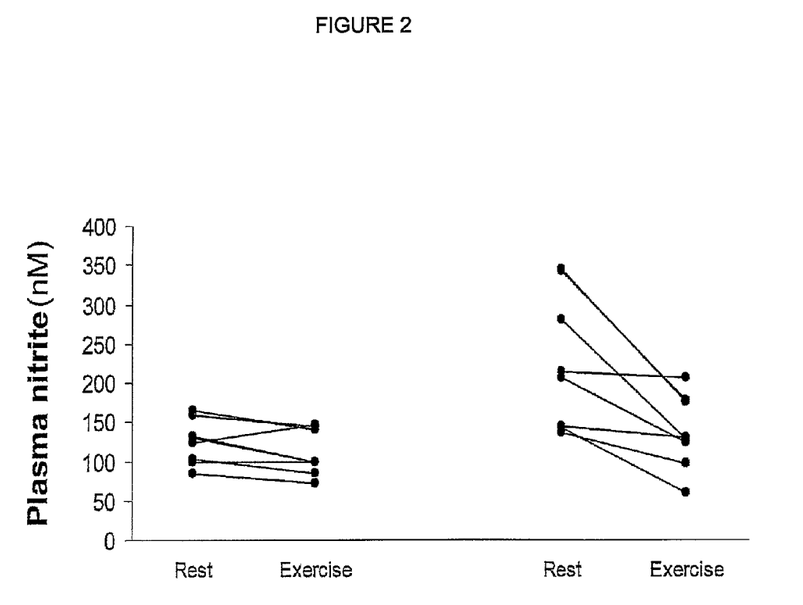
FIG. 2 illustrates the effects of a dietary supplementation with sodium nitrate or sodium chloride (placebo) on plasma concentrations of nitrite measured at rest and immediately after exercise in 9 healthy male volunteers.

Immediately after the maximal work test the nitrite levels were 111+/−29 in CON and 137+/−48 in NIT (p=0.17). The decrease in nitrite concentrations during exercise was more pronounced in NIT than in CON (See FIG. 2).

Figure 3:
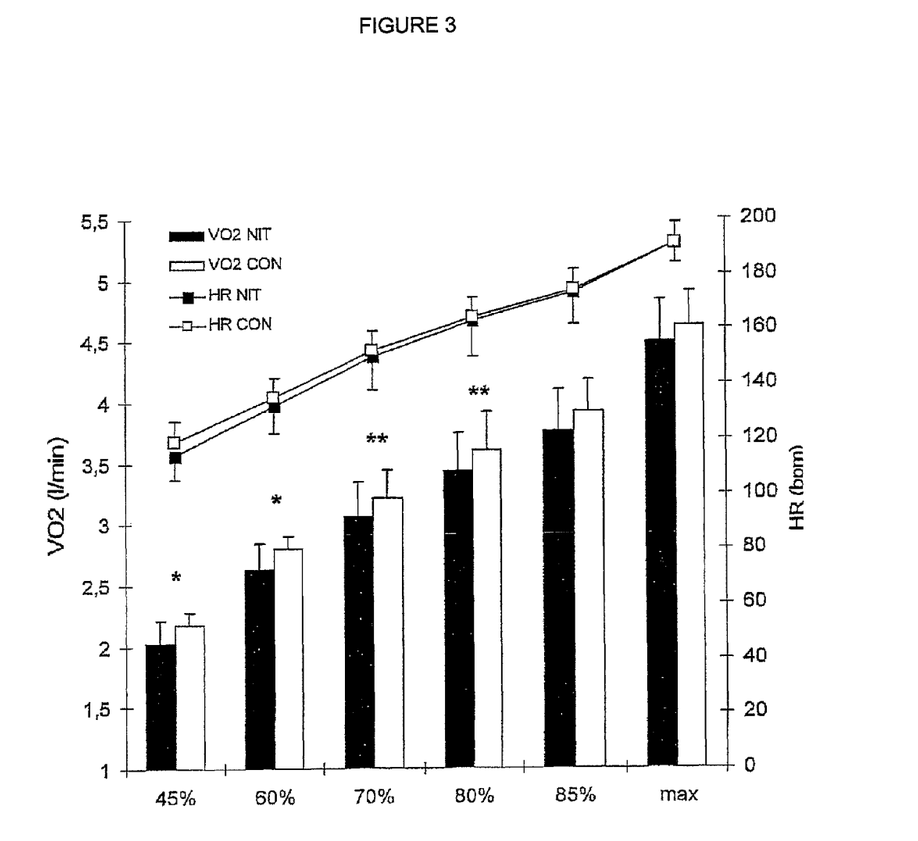
FIG. 3 shows oxygen consumption ($VO_2$) and heart rate (HR) measured at 6 different work rates after a 3-day dietary supplementation with sodium nitrate (0.1 mmol/kg/day, NIT) or an equal amount of sodium chloride (CON). The study had a randomized double-blind cross-over design with a washout period of at least 10 days between the tests. * $p<0.05$, ** $p<0.01$.
Figure 4:
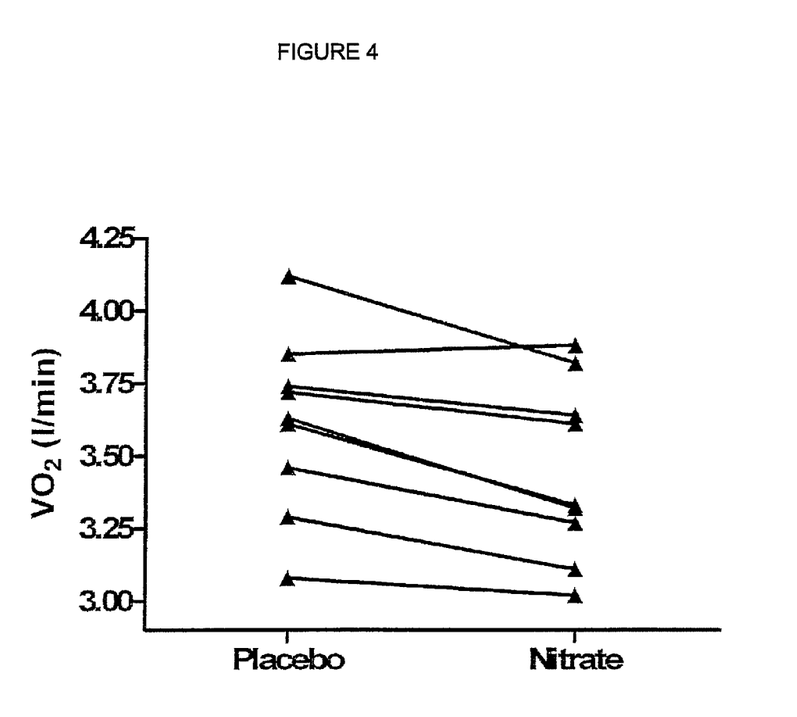
FIG. 4 shows oxygen consumption at 80% of $VO_{2peak}$ in 9 healthy male volunteers. Measurements were made after a 3-day dietary supplementation with nitrate (0.1 mmol/kg/day) or an equal amount of sodium chloride (placebo). The difference between nitrate and placebo periods was significant ($p<0.01$).
Figure 5:
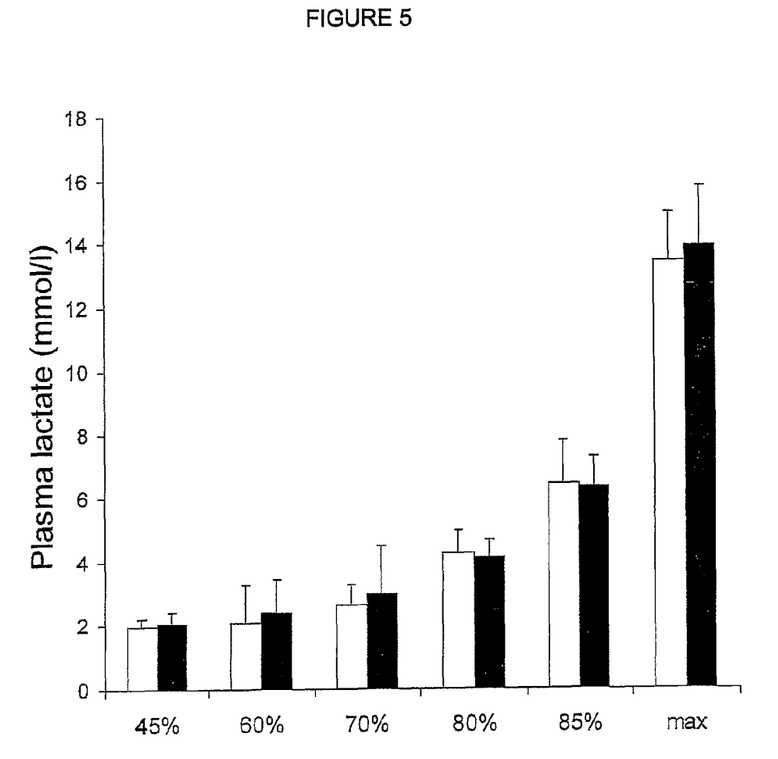
FIG. 5 shows plasma lactate concentration measured at 6 different work rates after dietary supplementation with sodium nitrate (0.1 mmol/kg/day for 3 days, filled bars) or an equal amount of sodium chloride (placebo, empty bars).

Work Parameters:

After nitrate administration $VO_2$ was significantly lower during the five work rates corresponding to 45-80% $VO_{2peak}$ compared to the placebo period (FIG. 3). The most significant difference was seen at 80% of $VO_{2peak}$ (NIT 3.44+/−0.31 l×min$^{-1}$ vs CON 3.61+/−0.31 l×min$^{-1}$, p=0.003, FIG. 4). On average $VO_2$ was 0.15 l×min$^{-1}$ lower in the NIT-trials over the five submaximal work rates. There was no difference in heart rate (HR) between the NIT and CON-trials (see FIG. 3). The oxygen pulse tended to decrease from 21.0+/−2.0 during CON to 20.3+/−1.9 ml×beat$^{-1}$ (p=0.08). No differences were found between NIT and CON in [HIa] (FIG. 5), $V_E$, $V_E/VO_2$ or respiratory exchange ratio (RER) during any of the submaximal work rates. The average gross efficiency improved from 19.7% during CON to 21.1% during NIT (p=0.02). Delta efficiency (DE) increased significantly from 22.1+/−1.6% during CON compared to 22.9+/−1.9% during NIT, (p=0.04).

At maximum work rate the $VO_{2peak}$ values for NIT and CON trials was 4.49+/−0.44 and 4.61+/−0.28 l×min$^{-1}$ respectively. No significant differences were noted either in $V_{Emax}$ (NIT 182+/−21.4 vs CON 186+/−21.7 l×min$^{-1}$, p=0.5), $HR_{max}$ (NIT 189.8+/−7.0 vs CON 190.3+/−7.5 beats×min$^{-1}$, p=0.94) or maximal work rate (NIT 360.6+/−32.8 vs CON 358.9+/−32.3 watt, p=0.35). There was no difference between NIT and CON in the rating of perceived exertion (Borg RPE-scale) at any work load (submax or max).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for non-therapeutically reducing oxygen consumption ($VO_2$) of a mammal and enhancing physical performance of the mammal during physical exercise, the method comprising:

orally administering inorganic nitrate and/or nitrite to said mammal up to three days prior to the mammal performing physical exercise and in a dose of about 0.01-10 mmol inorganic nitrate/kg bodyweight/day and/or of about 0.001-1 mmol inorganic nitrite/kg bodyweight/day; wherein administration of said inorganic nitrate and/or nitrite will result in reduced oxygen consumption ($VO_2$) in and enhanced physical performance of said mammal during the physical exercise as compared with the physical performance of said mammal during the physical exercise in the absence of administration of the inorganic nitrate and/or nitrite.

2. The method according to claim 1, wherein inorganic nitrate and nitrite are administered in a dose ratio interval of about 5:1 to about 100:1 (nitrate:nitrite).

3. The method according to claim 1, wherein inorganic nitrate is administered together with at least one polyphenol.

4. The method according to claim 1, wherein said mammal is a human, a horse, or a dog.

5. The method according to claim 4, wherein said mammal is a human.

6. The method according to claim 1, wherein inorganic nitrate is administered as an inorganic nitrate salt.

7. The method according to claim 6, wherein the inorganic nitrate salt is administered at a dose of about 0.1-1 mmol/kg bodyweight/day.

8. The method according to claim 1, wherein inorganic nitrite is administered as an inorganic nitrite salt.

9. The method according to claim 8, wherein the inorganic nitrite salt is administered at a dose of about 0.001-0.1 mmol/kg bodyweight/day.

10. The method according to claim 1, wherein the inorganic nitrate and/or nitrite is administered in a composition and said composition further comprises live bacteria capable of enhancing nitrate or nitrite reduction.

11. The method according to claim 1, wherein the inorganic nitrate and/or nitrite is administered in a composition and said composition further comprises an antibacterial compound.

12. The method according to claim 1, wherein the inorganic nitrate and/or nitrite is administered in a composition and said composition further comprises ethanol at a concentration of below about 5% (v/v).

13. The method according to claim 1, wherein the inorganic nitrate and/or nitrite is administered in a composition and said composition has a form selected from the group consisting of a liquid, a paste, a bar, a cake, a powder, a granulate, an effervescent tablet, a tablet, a capsule, a lozenge, a chewing gum, a fast melting tablet or wafer, a sublingual tablet, and a spray.

14. The method according to claim 1, wherein the inorganic nitrate and/or nitrite is administered in a composition and said composition is in the form of, or constitutes a part of, a food product selected from the group consisting of a liquid, a paste, a bar, a cake, a powder, and a granulate.

15. The method according to claim 1, wherein the source of inorganic nitrate is selected from the group consisting of a concentrate, a juice and an extract of at least one nitrate-containing vegetable.

16. The method according to claim 1, wherein inorganic nitrate is administered and the source of inorganic nitrate is selected from the group consisting of a concentrate, a juice and an extract of at least one nitrate-containing vegetable, wherein said vegetable is selected from the group consisting of green leafy vegetables, spinach, beetroot, fennel, lettuce, cabbage, and Chinese cabbage.

17. The method according to claim 16, wherein said vegetable is beetroot.

18. The method according to claim 1, wherein the inorganic nitrate and/or nitrite is administered in a composition and said composition further comprises an acidifying agent.

19. The method according to claim 18, wherein said acidifying agent is an artificial compound or a natural juice.

20. The method according to claim 19, wherein said natural juice is selected from the group consisting of lemon, lime, ascorbic acid, acetic acid, and vinegar from apple or grapes.

21. The method according to claim 1, wherein the inorganic nitrite and/or nitrate is administered in the form of a liquid and said liquid is a beetroot concentrate.

22. The method according to claim 1, wherein the inorganic nitrate and/or nitrite is administered in the form of a liquid and said liquid comprises a beetroot concentrate and acidifying agent.

23. The method according to claim 1, wherein administration of inorganic nitrate and/or nitrite results in an increase in muscular efficiency.

24. The method according to claim 1, wherein said inorganic nitrate and/or nitrite is administered to said mammal prior to or during exercise.

25. A method for non-therapeutically reducing oxygen consumption ($VO_2$) of a mammal and enhancing physical performance of the mammal during physical exercise, the method comprising:

orally administering inorganic nitrate and/or nitrite to said mammal in the dose of about 0.01-10 mmol inorganic nitrate/kg bodyweight/day or of about 0.001-1 mmol inorganic nitrite/kg bodyweight/day, and said mammal performing physical exercise, wherein said mammal exhibits reduced oxygen consumption ($VO_2$) and enhanced physical performance during the physical exercise as compared with the physical performance of said mammal during the physical exercise in the absence of administration of the inorganic nitrate and/or nitrite.

26. The method according to claim 25, wherein inorganic nitrate and nitrite are administered in a dose ratio interval of about 5:1 to about 100:1 (nitrate:nitrite).

27. The method according to claim 25, wherein inorganic nitrate is administered together with at least one polyphenol.

28. The method according to claim 25, wherein said mammal is a human, a horse, or a dog.

29. The method according to claim 28, wherein said mammal is a human.

30. The method according to claim 25, wherein inorganic nitrate is administered as an inorganic nitrate salt.

31. The method according to claim 30, wherein the inorganic nitrate salt is administered at a dose of about 0.1-1 mmol/kg bodyweight/day.

32. The method according to claim 25, wherein inorganic nitrite is administered as an inorganic nitrite salt.

33. The method according to claim 32, wherein the inorganic nitrite salt is administered at a dose of about 0.001-0.1 mmol/kg bodyweight/day.

34. The method according to claim 25, wherein the inorganic nitrate and/or nitrite is administered in a composition and said composition further comprises live bacteria capable of enhancing nitrate or nitrite reduction.

35. The method according to claim 25, wherein the inorganic nitrate and/or nitrite is administered in a composition and said composition further comprises an antibacterial compound.

36. The method according to claim 25, wherein the inorganic nitrate and/or nitrite is administered in a composition and said composition further comprises ethanol at a concentration of below about 5% (v/v).

37. The method according to claim 25, wherein the inorganic nitrate and/or nitrite is administered in a composition and said composition has a form selected from the group consisting of a liquid, a paste, a bar, a cake, a powder, a granulate, an effervescent tablet, a tablet, a capsule, a lozenge, a chewing gum, a fast melting tablet or wafer, a sublingual tablet, and a spray.

38. The method according to claim 25, wherein the inorganic nitrate and/or nitrite is administered in a composition and said composition is in the form of, or constitutes a part of, a food product selected from the group consisting of a liquid, a paste, a bar, a cake, a powder, and a granulate.

39. The method according to claim 25, wherein the source of inorganic nitrate is selected from the group consisting of a concentrate, a juice and an extract of at least one nitrate-containing vegetable.

40. The method according to claim 25, wherein inorganic nitrate is administered and the source of inorganic nitrate is selected from the group consisting of a concentrate, a juice and an extract of at least one nitrate-containing vegetable, wherein said vegetable is selected from the group consisting of green leafy vegetables, spinach, beetroot, fennel, lettuce, cabbage, and Chinese cabbage.

41. The method according to claim 40, wherein said vegetable is beetroot.

42. The method according to claim 25, wherein the inorganic nitrate and/or nitrite is administered in a composition and said composition further comprises an acidifying agent.

43. The method according to claim 42, wherein said acidifying agent is an artificial compound or a natural juice.

44. The method according to claim 43, wherein said natural juice is selected from the group consisting of lemon, lime, ascorbic acid, acetic acid, and vinegar from apple or grapes.

45. The method according to claim 25, wherein the inorganic nitrite and/or nitrate is administered in the form of a liquid and said liquid is a beetroot concentrate.

46. The method according to claim 25, wherein the inorganic nitrite and/or nitrate is administered in the form of a liquid and said liquid comprises a beetroot concentrate and acidifying agent.

47. The method according to claim 25, wherein administration of inorganic nitrate and/or nitrite results in an increase in muscular efficiency.

48. The method according to claim 25, wherein said inorganic nitrate and/or nitrite is administered to said mammal prior to or during exercise.

49. The method according to claim 1, further comprising said mammal performing physical exercise within about 60 minutes of the administration of inorganic nitrate and/or nitrite.

50. The method according to claim 1, wherein the enhanced physical performance of said mammal during the physical exercise is measured as increased Gross efficiency (GE) and/or increased Delta efficiency (DE).

51. The method according to claim 25, further comprising said mammal performing physical exercise within about 60 minutes of the administration of inorganic nitrate and/or nitrite.

52. The method according to claim 25, wherein the enhanced physical performance of said mammal during the physical exercise is measured as increased Gross efficiency (GE) and/or increased Delta efficiency (DE).

* * * * *

UNITED STATES PATENT AND TRADEMARK OFFICE
CERTIFICATE OF CORRECTION

| | | |
|---|---|---|
| PATENT NO. | : 9,180,140 B2 | Page 1 of 1 |
| APPLICATION NO. | : 12/528798 | |
| DATED | : November 10, 2015 | |
| INVENTOR(S) | : Lundberg et al. | |

It is certified that error appears in the above-identified patent and that said Letters Patent is hereby corrected as shown below:

On The Title Page, at (45), change "*Nov." to --Nov.--.

On The Title Page, at (*), delete "This patent is subject to terminal disclaimer.".

Signed and Sealed this
Fifth Day of April, 2016

Michelle K. Lee
*Director of the United States Patent and Trademark Office*